United States Patent [19]

Wenger et al.

[11] Patent Number: 5,017,211
[45] Date of Patent: May 21, 1991

[54] HETEROCYCLIC COMPOUNDS

[75] Inventors: Jean Wenger, Uster; Paul Winternitz, Greifensee; Martin Zeller, Dübendorf, all of Switzerland

[73] Assignee: Ciba-Geigy Corporation, Ardsley, N.Y.

[21] Appl. No.: 362,417

[22] PCT Filed: Sep. 19, 1988

[86] PCT No.: PCT/CH88/00163

§ 371 Date: May 19, 1989

§ 102(e) Date: May 19, 1989

[87] PCT Pub. No.: WO89/02891

PCT Pub. Date: Apr. 6, 1989

[30] Foreign Application Priority Data

Sep. 23, 1987 [CH] Switzerland ............... 3677/87

[51] Int. Cl.$^5$ ............... A01N 43/48; C07D 239/54
[52] U.S. Cl. ............................. 71/92; 540/601; 544/60; 544/123; 544/232; 544/283; 544/284; 544/285; 544/295; 544/310; 544/311; 544/312; 544/313
[58] Field of Search ............ 544/232, 283, 284, 285, 544/310, 311, 312, 313; 71/92

[56] References Cited

U.S. PATENT DOCUMENTS

| | | | |
|---|---|---|---|
| 3,235,357 | 2/1966 | Loux | 544/309 |
| 3,235,360 | 2/1966 | Soboczenski | 544/309 |
| 3,235,363 | 2/1966 | Luckenbaugh et al. | 544/309 |
| 3,291,592 | 12/1966 | Evans | 544/309 |
| 3,346,207 | 10/1967 | Jenny | 242/45 |
| 3,352,862 | 11/1967 | Loux | 544/309 |
| 3,360,520 | 12/1967 | Luckenbaugh et al. | 544/309 |
| 4,746,352 | 5/1988 | Wenger et al. | 544/311 |
| 4,760,163 | 7/1988 | Wenger et al. | 544/311 |

FOREIGN PATENT DOCUMENTS

| | | |
|---|---|---|
| 968661 | 9/1964 | United Kingdom |
| 968666 | 9/1964 | United Kingdom |
| 1035096 | 7/1966 | United Kingdom |
| 1035097 | 7/1966 | United Kingdom |
| 1035098 | 7/1966 | United Kingdom |
| 1257259 | 12/1971 | United Kingdom |

OTHER PUBLICATIONS

Wenger et al., CA 106-50241g (1987).
Wenger et al., Chem. Abst. 109-231048g (1988).
Wenger et al., Chem. Abst. 109-73464h (1988).
Wenger et al., Chem. Abst. 111-134187k (1989).

Primary Examiner—Cecilia Shen
Attorney, Agent, or Firm—Edward M. Roberts

[57] ABSTRACT

The invention is concerned with novel compounds of the formula

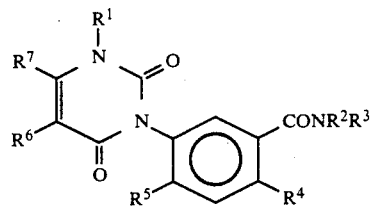

I wherein $R^1$, $R^2$, $R^3$, $R^4$, $R^5$, $R^6$ and $R^7$ have the significances given in the description, as well as enol ethers and salts thereof and their manufacture, weed control compositions which contain such compounds as the active substance and the use of the active substances or compositions for the control of weeds. The invention is also concerned with certain novel starting materials and their production.

12 Claims, No Drawings

HETEROCYCLIC COMPOUNDS

The present invention is concerned with heterocyclic compounds, namely 3-aryluracils of the general formula

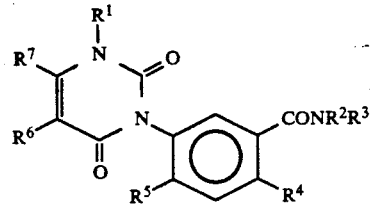

I wherein
$R^1$ signifies hydrogen, $C_{1-4}$-alkyl, $C_{1-4}$-haloalkyl, $C_{3\ or\ 4}$-alkenyl or $C_{3\ or\ 4}$-alkynyl, $R^2$ and $R^3$ each independently signify hydrogen, $C_{1-8}$-alkyl, $C_{2-8}$-alkenyl, $C_{3-8}$-alkynyl, $C_{1-8}$-haloalkyl, $C_{1-8}$-hydroxyalkyl, $C_{1-4}$-alkoxy-$C_{1-8}$-alkyl, $C_{1-4}$-alkylthio-$C_{1-8}$-alkyl, $C_{1-4}$-haloalkoxy-$C_{1-8}$-alkyl, $C_{2-8}$-cyanoalkyl, $C_{1-8}$-nitroalkyl, $C_{2-9}$-carboxyalkyl, $C_{2-5}$-alkoxycarbonyl-$C_{1-8}$-alkyl, $C_{1-4}$-alkylsulphonyl-$C_{1-8}$-alkyl, di($C_{1-4}$-alkyl)-phosphono-$C_{1-8}$-alkyl, $C_{3-8}$-cycloalkyl, $C_{1-8}$-alkoxy or phenyl or phenyl-$C_{1-4}$-alkyl optionally substituted with halogen, hydroxy, $C_{1-4}$-alkyl, $C_{1-4}$-haloalkyl, $C_{1-4}$-alkoxy, $C_{1-4}$-alkylthio, $C_{1-4}$-haloalkoxy, cyano, nitro, carboxy and/or $C_{2-5}$-alkoxycarbonyl, whereby this optionally substituted phenyl can have a fused, saturated, carbocyclic five- to seven-membered ring or a fused, saturated, heterocyclic five- to seven-membered ring containing 1 or 2 oxygen atoms, whereby $R^2$ and $R^3$ cannot both stand for $C_{1-8}$-alkoxy, or $R^2$ and $R^3$ together with the nitrogen atom to which they are attached signify a four- to seven-membered heterocyclic ring which is optionally mono- or multiply substituted with $C_{1-6}$-alkyl and which, in addition to the nitrogen atom, can also have in the ring an oxygen atom, a sulphur atom and/or a second nitrogen atom, $R^4$ signifies halogen or cyano,
$R^5$ signifies hydrogen or halogen,
$R^6$ signifies hydrogen, halogen or $C_{1-4}$-alkyl,
$R^7$ signifies $C_{1-4}$-alkyl or, where $R^1$ is different from $C_{1-4}$-haloalkyl, also $C_{1-4}$-haloalkyl, or
$R^6$ and $R^7$ together signify tri- or tetramethylene, and the corresponding enol ethers of those compounds of formula I in which $R^1$ signifies $C_{1-4}$-alkyl, $C_{3\ or\ 4}$-alkenyl or $C_{3\ or\ 4}$-alkynyl, $R^6$ signifies hydrogen, halogen or $C_{1-4}$-alkyl and $R^7$ signifies $C_{1-4}$-haloalkyl, as well as salts of those compounds of formula I or enol ethers in which $R^1$ and/or $R^2$ signify hydrogen.

The above-mentioned enol ethers are thus the compounds of the formula

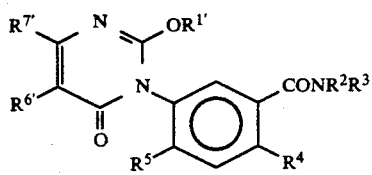

Ia wherein $R^2$, $R^3$, $R^4$ and $R^5$ have the significances given above and $R^{1'}$ signifies $C_{1-4}$-alkyl, $C_{3\ or\ 4}$-alkenyl or $C_{3\ or\ 4}$-alkynyl, $R^{6'}$ signifies hydrogen, halogen or $C_{1-4}$-alkyl and $R^{7'}$ signifies $C_{1-4}$-haloalkyl. Their salts are salts of those enol ethers Ia in which $R^2$ signifies hydrogen.

The compounds in accordance with the invention have herbicidal activity and are suitable as active substances of weed control compositions. Accordingly, the invention also embraces weed control compositions which contain compounds in accordance with the invention as the active substance, a process for the manufacture of these compounds as well as the use of the compounds or compositions for the control of weeds.

In formula I above "halogen" embraces fluorine, chlorine, bromine and iodine. The alkyl, alkenyl and alkynyl residues can be straight-chain or branched, whereby this also applies to the alkyl part or the alkyl parts of the haloalkyl, hydroxyalkyl, alkoxyalkyl, alkylthioalkyl, haloalkoxyalkyl, cyanoalkyl, nitroalkyl, carboxyalkyl, alkoxycarbonyl, alkylsulphonylalkyl, dialkylphosphonoalkyl, alkoxy, haloalkoxy and phenylalkyl groups. A haloalkyl or haloalkoxy group can have one or more (similar or different) halogen atoms. Likewise, a substituted phenyl or phenylalkyl group can have one or more of the aforementioned substituents which can be the same or different. Under "lower alkyl" mentioned hereinafter there is to be understood especially $C_{1-6}$-alkyl.

Examples of bicyclic groups which $R^2$ and $R^3$ can signify are 1,3-benzodioxol-5-yl and 1,3-benzodioxan-6-yl.

Examples of four- to seven-membered heterocyclic rings which $NR^2R^3$ can form are pyrrolidino, piperidino, hexahydroazepino, morpholino, thiomorpholino, piperazino and 4-methylpiperazino.

The salts of the compounds of formula I and of their enol ethers are especially alkali metal salts, e.g. sodium and potassium salts; alkaline earth metal salts, e.g. calcium and magnesium salts; ammonium salts, i.e. unsubstituted ammonium salts and mono- or multiply-substituted ammonium salts, e.g. triethylammonium and methylammonium salts, as well as salts with other organic bases, e.g. with pyridine.

The presence of at least one asymmetric carbon atom in the compounds of formula I and in their enol ethers means that the compounds can occur in optically isomeric forms. Geometric isomerism can also occur when an aliphatic C═C double bond is present. Moreover, in those compounds of formula I in which $R^1$ signifies hydrogen it is not to be excluded that keto-enol tautomerism [—NH—CO—⇌—N═C(OH)—] occurs. Formula I is intended to embrace all of these possible isomeric forms as well as mixtures thereof.

When $R^1$ signifies alkenyl or alkynyl, this residue is preferably allyl or propargyl. In general, a halogen atom which may be present is preferably fluorine, chlorine or bromine. A haloalkyl group which may be present is preferably difluoromethyl, trifluoromethyl or pentafluoroethyl.

A particular group of compounds of formula I comprises those compounds I in which $R^1$ signifies hydrogen, $C_{1-4}$-alkyl or $C_{1-4}$-haloalkyl, $R^2$ signifies hydrogen or $C_{1-8}$-alkyl, $R^3$ signifies hydrogen, $C_{1-8}$-alkyl, $C_{2-8}$-alkenyl, $C_{3-8}$-alkynyl, $C_{1-8}$-haloalkyl, $C_{1-8}$-hydroxyalkyl, $C_{2-8}$-cyanoalkyl, $C_{2-5}$-alkoxycarbonyl-$C_{1-8}$-alkyl, $C_{3-8}$-cycloalkyl, $C_{1-8}$-alkoxy, phenyl optionally substituted with halogen, $C_{1-4}$-alkyl, $C_{1-4}$-haloalkyl, $C_{1-4}$-haloalkoxy and/or $C_{2-5}$-alkoxycarbonyl, whereby this optionally substituted phenyl can have a fused, saturated, heterocyclic five- or six-membered ring containing 2 oxygen atoms, or phenyl-$C_{1-4}$-alkyl optionally substituted with nitro, $R^4$ signifies halogen and $R^6$ signifies halogen or $C_{1-4}$-alkyl, and the enol ethers of these compounds.

Independently of each other $R^1$ preferably signifies $C_{1-4}$-alkyl, especially methyl, or $C_{1-4}$-fluoroalkyl, especially difluoromethyl; $R^2$ preferably signifies hydrogen or $C_{1-8}$-alkyl; $R^3$ preferably signifies $C_{1-8}$-alkyl, $C_{2-8}$-alkenyl, $C_{3-8}$-alkynyl, $C_{2-8}$-cyanoalkyl, $C_{3-8}$-cycloalkyl or benzyl; $R^4$ preferably signifies halogen, especially chlorine or bromine; $R^5$ preferably signifies hydrogen or fluorine; $R^6$ preferably signifies hydrogen, fluorine or methyl; and $R^7$ preferably signifies $C_{1-4}$-alkyl, especially methyl, or $C_{1-4}$-haloalkyl, especially trifluoromethyl or pentafluoroethyl.

Especially preferred individual compounds in accordance with the invention are the ethyl-, n-propyl-, isopropyl-, n-butyl-, sec.butyl-, allyl-, 2-methyl-2-propenyl-, propargyl-, 1,1-dimethyl-2-propynyl-, 1-cyano-1-methylethyl-, 1-cyano-1,2-dimethylpropyl-, cyclopropyl-, cyclohexyl-, benzyl- and 1-phenylethylamide of 2-chloro-5-[3,6-dihydro-2,6-dioxo-3-methyl-4-trifluoromethyl-1(2H)-pyrimidinyl]-4-fluorobenzoic acid, N,N-diethyl-2-chloro-5-[3,6-dihydro-2,6-dioxo-3-methyl-4-trifluoromethyl-1(2H)-pyrimidinyl]-4-fluorobenzamide, the allyl- and 1-cyano-1-methylethylamide of 2-chloro-5-[3,6-dihydro-3,4-dimethyl-2,6-dioxo-1(2H)-pyrimidinyl]-4-fluorobenzoic acid, N-allyl-2-chloro-5-[3,6-dihydro-2,6-dioxo-3-methyl-4-pentafluoroethyl-1(2H)-pyrimidinyl]-4-fluorobenzamide, N-allyl-2-chloro-5-[3-difluoromethyl-3,6-dihydro-2,6-dioxo-4-methyl-1(2H)-pyrimidinyl]-4-fluorobenzamide and N-allyl-2-chloro-5-[3,6-dihydro-3,4-dimethyl-2,6-dioxo-1(2H)-pyrimidinyl]-benzamide.

Further representatives of compounds in accordance with the invention are the methyl-, n-pentyl-, n-hexyl-, n-octyl-, cyanomethyl- and cyclopropylamide of 2-chloro-5-[3,6-dihydro-2,6-dioxo-3-methyl-4-trifluoromethyl-1(2H)-pyrimidinyl]-4-fluorobenzoic acid and the ethyl-, n-propyl-, isopropyl-, n-butyl-, sec.butyl-, 2-methyl-2-propenyl-, propargyl-, 1,1-dimethyl-2-propynyl-, cyanomethyl-, 1-cyano-1-methylethyl-, cyclopropyl-, cyclopentyl-, cyclohexyl- and benzylamide of 2-chloro-5-[3,6-dihydro-3,4-dimethyl-2,6-dioxo-1(2H)-pyrimidinyl]-4-fluorobenzoic acid, of 2-chloro-5-[3,6-dihydro-3-difluoromethyl-2,6-dioxo-4-methyl-1(2H)-pyrimidinyl]-4-fluorobenzoic acid, of 2-chloro-5-[3,6-dihydro-2,6-dioxo-3-methyl-4-pentafluoroethyl-1(2H)-pyrimidinyl]-4-fluorobenzoic acid and of 2-chloro-5-[3,6-dihydro-2,6-dioxo-3-methyl-4-trifluoromethyl-1(2H)-pyrimidinyl]-benzoic acid.

The process in accordance with the invention for the manufacture of the compounds of formula I and their enol ethers as well as salts is characterized by (a) for the manufacture of those compounds of formula I in which $R^1$ signifies hydrogen, reacting a compound of the general formula

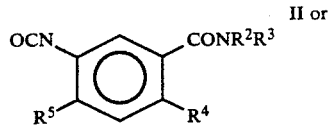

II or

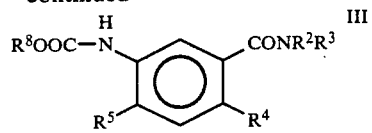

III wherein $R^2$, $R^3$, $R^4$ and $R^5$ have the significances given above and $R^8$ signifies lower alkyl, preferably $C_{1-4}$-alkyl, with the deprotonized form of a compound of the general formula

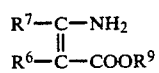

IV wherein $R^6$ and $R^7$ have the significances given above and $R^9$ signifies lower alkyl, preferably $C_{1-4}$-alkyl, (b) for the manufacture of those compounds of formula I in which $R^1$ signifies hydrogen, reacting a compound of the general formula

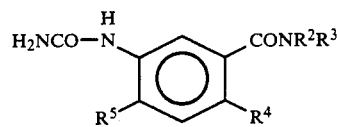

V wherein $R^2$, $R^3$, $R^4$ and $R^5$ have the significances given above, with a compound of the general formula

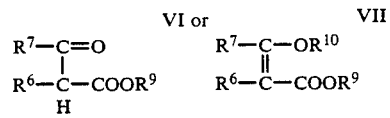

VI or VII wherein $R^6$, $R^7$ and $R^9$ have the significances given above and $R^{10}$ signifies lower alkyl, preferably $C_{1-4}$-alkyl, (c) for the manufacture of those compounds of formula I in which $R^1$ signifies $C_{1-4}$-alkyl, $C_{1-4}$-haloalkyl, $C_{3\ or\ 4}$-alkenyl or $C_{3\ or\ 4}$-alkynyl, appropriately alkylating a compound of the general formula

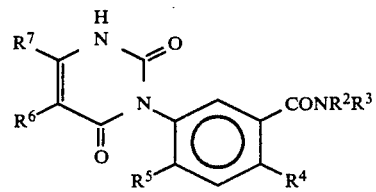

I' wherein $R^2$, $R^3$, $R^4$, $R^5$, $R^6$ and $R^7$ have the significances given above, (d) for the manufacture of the enol ethers of the compounds of formula I in which neither $R^2$ nor $R^3$ signifies hydrogen, treating a compound of the general formula

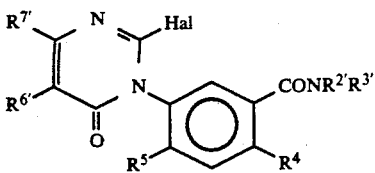

VIIIa wherein $R^4$, $R^5$, $R^{6'}$ and $R^{7'}$ have the significances given above, $R^{2'}$ and $R^{3'}$ have the significances of $R^2$ and $R^3$ given above with the exception of hydrogen and Hal signifies chlorine or bromine, with the deprotonized form of an alkanol, alkenol or alkynol $R^{1'}OH$ in which $R^{1'}$ signifies $C_{1-4}$-alkyl, $C_{3\ or\ 4}$-alkenyl or $C_{3\ or\ 4}$-alkynyl, or (e) for the manufacture of those compounds of formula I in which $R^1$ signifies $C_{1-4}$-alkyl, $C_{1-4}$-haloalkyl, $C_{3\ or\ 4}$-alkenyl or $C_{3\ or\ 4}$-alkynyl and of the enol ethers of those compounds of formula I in which $R^1$ signifies $C_{1-4}$-alkyl, $C_{3\ or\ 4}$-alkenyl or $C_{3\ or\ 4}$-alkynyl, $R^6$ signifies hydrogen, halogen or $C_{1-4}$-alkyl and $R^7$ signifies $C_{1-4}$-haloalkyl, reacting a benzoic acid of the general formula

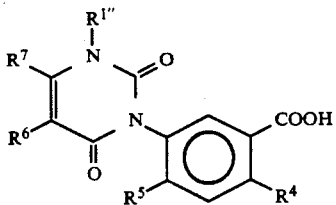

IX wherein $R^4$, $R^5$, $R^6$ and $R^7$ have the significances given above and $R^{1''}$ signifies $C_{1-4}$-alkyl, $C_{1-4}$-haloalkyl, $C_{3\ or\ 4}$-alkenyl or $C_{3\ or\ 4}$-alkynyl, or the respective enol ether, i.e. of the formula

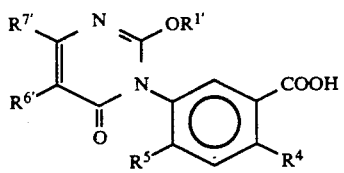

IXa wherein $R^{1'}$, $R^4$, $R^5$, $R^{6'}$ and $R^{7'}$ have the significances given above, whereby the benzoic acid or its enol ether can be present in the form of a reactive derivative, with an amine of the general formula $HNR^2R^3$      X wherein $R^2$ and $R^3$ have the significances given above, and, if desired, converting a thus-obtained compound of formula I in which $R^1$ and/or $R^2$ signifies hydrogen or a thus-obtained enol ether in which $R^2$ signifies hydrogen into a salt.

In process variant (a) the deprotonized form of the compound of formula IV is the product obtained by treating this compound IV with a base such as an alkali metal or alkaline earth metal alcoholate, e.g. sodium ethanolate, potassium isopropylate, potassium isobutylate or potassium sec.-butylate, or an alkali metal hydride, e.g. sodium hydride; with an alkali metal amide, e.g. lithium amide or sodamide; with an alkali metal, e.g. lithium or sodium; or with an organometallic compound such as an alkyllithium, e.g. methyllithium or butyllithium, or phenyllithium. This treatment is conveniently effected in an inert organic diluent such as an aromatic hydrocarbon, e.g. benzene, toluene or a xylene; a heterocyclic solvent, e.g. N-methylpyrrolidone, pyridine or quinoline; dimethylformamide; or dimethyl sulphoxide. The 3-isocyanatobenzamide of formula II or the 3-alkoxycarbonylaminobenzamide of formula III is then reacted with the thus-produced deprotonized form of the compound IV conveniently in the same diluent in which the deprotonization has been carried out, generally at reaction temperatures in the range of about $-100°$ C. to 200° C., preferably at $-70°$ C. to 20° C. (compound II) or in the range of about 50° C. to 200° C., preferably at 100° C. to 160° C. (compound III).

The reaction according to process variant (b) is conveniently effected in an essentially anhydrous diluent as well as in the presence of an acidic catalyst at an elevated temperature. Especially suitable diluents are organic solvents which form azeotropes with water, such as cyclic hydrocarbons, e.g. cyclohexane; aromatics, e.g. benzene, toluene and xylenes; halogenated hydrocarbons, e.g. methylene chloride, chloroform, carbon tetrachloride and chlorobenzene; and aliphatic or cyclic ethers, e.g. 1,2-dimethoxyethane, tetrahydrofuran and dioxan. As acidic catalysts there especially come into consideration strong mineral acids such as sulphuric acid and hydrochloric acid; organic acids such as p-toluenesulphonic acid; phosphorus-containing acids such as orthophosphoric acid and polyphosphoric acid; and acidic cation exchangers such as "Amberlyst 15" (Fluka). The reaction is generally carried out in a temperature range of about 50° C. to 130° C., preferably at the reflux temperature of the reaction mixture. Under these reaction conditions the desired rapid removal of the water formed in the reaction is achieved.

In process variant (c) the term "alkylating" stands for the substitution of the hydrogen atom of the $N^1$-atom of the uracil nucleus with a $C_{1-4}$-alkyl, $C_{1-4}$-haloalkyl, $C_{3\ or\ 4}$-alkenyl or $C_{3\ or\ 4}$-alkynyl group. A $C_{1-4}$-alkyl, $C_{3\ or\ 4}$-alkenyl or $C_{3\ or\ 4}$-alkenyl halide, especially the chloride, bromide or iodide, or-in the case of a N-$C_{1-4}$-alkyl substitution-a di($C_{1-4}$-alkyl) sulphate is conveniently used as the alkylating agent. The alkylation is conveniently carried out in the presence of an inert organic solvent, optionally in admixture with water, as well as in the presence of a base. Suitable inert organic solvents are protic solvents such as lower alkanols, e.g. methanol and ethanol; aprotic solvents such as aliphatic or cyclic ethers, e.g. diethyl ether, 1,2-dimethoxyethane, tetrahydrofuran and dioxan, and lower aliphatic ketones, e.g. acetone and 2-butanone; or polar solvents such as dimethylformamide, dimethyl sulphoxide and acetonitrile, and suitable bases are metal hydrides, e.g. sodium hydride; alkali metal alcoholates, e.g. sodium ethanolate; or alkali metal carbonates and bicarbonates, e.g. sodium carbonate, potassium carbonate, sodium bicarbonate and potassium bicarbonate. The reaction temperatures conveniently lie between 0° C. and the reflux temperature of the reaction mixture.

The deprotonized form of the alkanol, alkenol or alkynol $R^{1'}OH$ is used in process variant (d) conveniently results either by using the hydroxy compound $R^{1'}OH$ in the presence of an organic base, especially an organic tertiary base such as triethylamine or pyridine or the corresponding metal alcoholate, alkenolate or alkynolate $R^{1'}O^{\ominus}M^{\oplus}$ in which $M^{\oplus}$ signifies an equivalent of a metal ion such as an alkali metal ion, e.g. sodium or potassium, or an alkaline earth metal ion, e.g. calcium or magnesium. The sodium ion is the preferred metal ion. The reaction is conveniently effected in an excess of the corresponding hydroxy compound $R^{1'}OH$ as the diluent and at temperatures between 0° C. and 50° C., preferably at room temperature.

Process variant (e) is an amidation of the benzoic acid IX or of the enol ether IXa or of a reactive derivative of the acid or of the enol ether. This amidation can be carried out according to methods known per se. Thus, for example, an acid halide, especially the acid chloride, of the benzoic acid IX or of the enol ether IXa is reacted with the amine X in an inert organic diluent such as an aliphatic or cyclic ether, e.g. diethyl ether, 1,2-dimethoxyethane, tetrahydrofuran or dioxan; a chlorinated aliphatic hydrocarbon, e.g. methylene chloride, 1,2-dichloroethane or chloroform; or an aliphatic or aromatic hydrocarbon, e.g. n-hexane, benzene, toluene or a xylene, at temperatures between −20° C. and the reflux temperature of the reaction mixture. The reaction can be effected with or without the addition of a base such as a tertiary amine, e.g. triethylamine, pyridine or quinoline; an alkali metal carbonate, e.g. sodium or potassium carbonate; or excess amine X.

Insofar as they are not produced directly according to those of the process variants described above which are carried out under basic reaction conditions, the desired salts of the compounds I and enol ethers in accordance with the invention in which $R^1$ and/or $R^2$ signifies hydrogen can be manufactured from these in a manner known per se such as, for example, by dissolving the compound I or the enol ether in a solution of an inorganic or organic base. The salt formation is generally effected within a short time at room temperature. In one embodiment the sodium salt is manufactured by dissolving the uracil derivative I in aqueous sodium hydroxide solution at room temperature, with equivalent amounts of the uracil derivative and of sodium hydroxide being used. The solid salt can then be isolated by precipitation with a suitable inert solvent or by evaporation of the solvent. A further embodiment comprises introducing an aqueous solution of an alkali metal salt of the uracil derivative I into an aqueous solution of a salt which has a metal ion other than an alkali metal ion, whereby the second metal salt of the uracil derivative is manufactured. This embodiment generally serves for the manufacture of uracil metal salts which are insoluble in water.

The resulting compounds of formula I, enol ethers as well as salts can be isolated and purified according to methods known per se. Insofar as no planned synthesis for the isolation of pure isomers is carried out, the product can result as a mixture of two or more isomers. The isomers can be separated according to methods known per se. If desired, pure optically active isomers can also be manufactured, for example, by synthesis from corresponding optically active starting materials.

The starting materials of formulae II, III and V, which are novel, can be produced in a manner known per se, e.g. in accordance with Reaction Scheme 1 hereinafter in which $R^2$, $R^3$, $R^4$, $R^5$ and $R^8$ have the significances given above and $R^{11}$ signifies a leaving group such as halogen, e.g. chlorine, imidazolyl, triazolyl or acyloxy, e.g. acetoxy, and $M'^{\oplus}$ signifies an alkali metal ion, especially the sodium ion:

Reaction Scheme 1

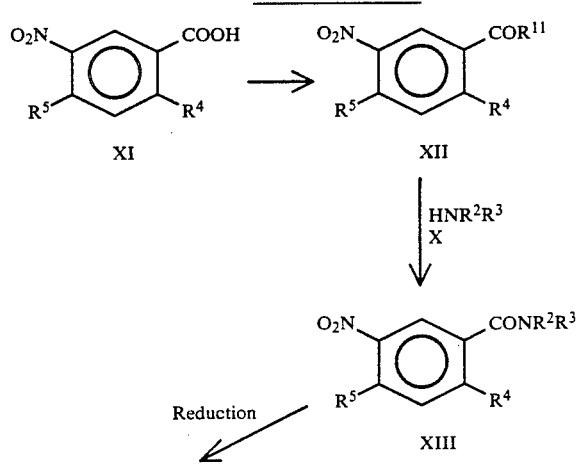

Reaction Scheme 1

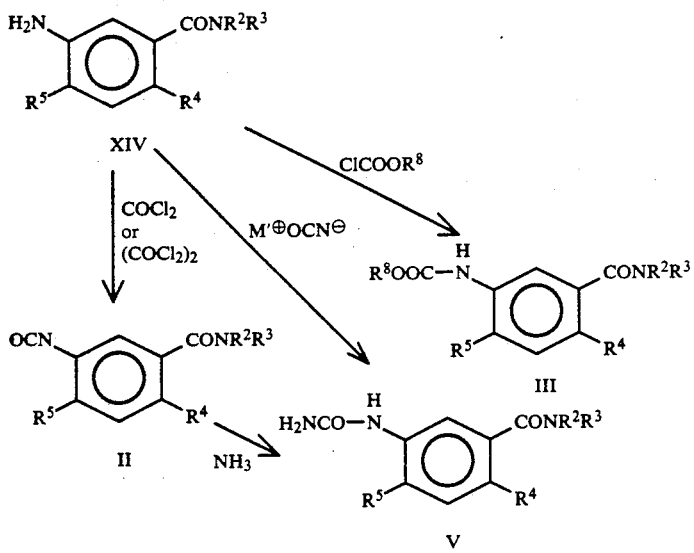

The conversion of the benzoic acid of formula XI into its reactive derivative of formula XII is effected according to methods known per se. Thus, for example, in the production of an acid halide of the benzoic acid (formula XII in which $R^{11}$ signifies halogen, e.g. chlorine), this is treated with a halogenating agent such as, for example, thionyl chloride or phosphorus pentachloride, optionally in an inert organic solvent such as an optionally halogenated, especially chlorinated, hydrocarbon, e.g. benzene or carbon tetrachloride, at temperatures between −20° C. and 150° C. Benzoic anhydrides of formula XII ($R^{11}$ signifies acyloxy, e.g. acetoxy) can be produced, for example, by reacting the benzoic acid XI or an alkali metal or alkaline earth metal salt thereof, e.g. the sodium or potassium salt, with an acyl chloride, e.g. acetyl chloride, at temperatures between −20° C. and 150° C.

The derivative XII is subsequently converted into the benzamide XIII with the amine X for example analogously to process variant (e) described above, whereby water can also be used as the diluent.

The reduction of the 3-nitrobenzamide XIII to the corresponding 3-aminobenzamide of formula XIV is effected, for example, using iron, zinc, tin or tin chloride or by catalytic hydrogenation. For example, the 3-nitrobenzamide XIII in an organic solvent such as a lower alkanol, e.g. methanol or ethanol, a lower alkanoic acid, e.g. acetic acid, or an aliphatic or cyclic ether, e.g. tetrahydrofuran or dioxan, in water or in a mixture of an organic solvent with water is treated with a metal, e.g. iron, zinc or tin, or a metal salt of lower oxidation state, e.g. tin(II) chloride. The reaction is conveniently effected in the presence of an acid such as hydrochloric acid, sulphuric acid, orthophosphoric acid or acetic acid; there are generally used between 0.01 and 20 molar equivalents of acid based on the amount of 3-nitrobenzamide XIII used. The reaction temperatures conveniently lie between −20° C. and 150° C. Alternatively, the 3-nitrobenzamide can be hydrogenated in an organic solvent such as a lower alkanol, e.g. methanol or ethanol, or a lower alkanoic acid, e.g. acetic acid, at temperatures between 0° C. and 100° C., under elevated pressure up to 100 atm. and in the presence of a transition metal, e.g. platinum or palladium, as the catalyst.

The thus-produced 3-aminobenzamide XIV can then be converted, according to choice, into a 3-isocyanatobenzamide of formula II, into a 3-alkoxycarbonylaminobenzamide of formula III or into a 3-ureidobenzamide of formula V.

For the production of the 3-isocyanatobenzamide II, the 3-aminobenzamide XIV is reacted with phosgene or diphosgene, conveniently in an inert diluent such as ethyl acetate, toluene or a xylene at temperatures of 0° C. to 150° C., preferably 30° C. to 80° C.

The conversion of the 3-aminobenzamide XIV into the 3-alkoxycarbonylaminobenzamide III is conveniently effected with a lower alkyl chloroformate, especially the ethyl ester, in an organic solvent such as an aliphatic or cyclic ether, e.g. diethyl ether, tetrahydrofuran or dioxan, a chlorinated aliphatic hydrocarbon, e.g. methylene chloride or chloroform, in water or in a mixture of an organic solvent and water at temperatures between −20° C. and 100° C. and in the presence of an inorganic base such as an alkali metal or alkaline earth metal hydroxide, e.g. sodium hydroxide, or an organic base, e.g. triethylamine, pyridine or quinoline. When an organic base is used, this can also serve as the solvent. In a preferred embodiment the reaction is carried out in a tertiary amine, e.g. pyridine, as the solvent and in a temperature range of 0° C. to 30° C.

The 3-aminobenzamide XIV is reacted with an alkali metal cyanate $M'^{\oplus}OCN^{\ominus}$, especially with sodium cyanate, conveniently in water at temperatures between 0° C. and 50° C. and in the presence of an inorganic acid, e.g. hydrochloric acid or sulphuric acid, or of an organic acid, e.g. acetic acid, to give a 3-ureidobenzamide V. Alternatively, the 3-isocyanatobenzamide II can be converted into the 3-ureidobenzamide V using ammonia in an inert organic solvent such as an aliphatic or cyclic ether, e.g. diethyl ether, tetrahydrofuran or dioxan, an aromatic hydrocarbon, e.g. toluene, or water and at temperatures between −20° C. and 50° C.

Certain starting materials and intermediates of formulae XIII, XIV, II, III and V, namely the compounds of the general formula

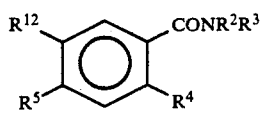

wherein $R^2$, $R^3$, $R^4$ and $R^5$ have the significances given above, $R^{12}$ signifies nitro, amino, isocyanato, a lower alkoxycarbonyl group $R^8OOCNH$ or ureido and $R^8$ has the significance given above, whereby $R^5$ can only stand for fluorine where $R^{12}$ signifies nitro or amino, are novel and form a further object of the present invention.

The starting materials of formula I' which are used in process variant (c) are a sub-group of compounds of formula I which correspond to the products of process variant (a) or (b).

The starting materials of formulae VIIIa, which are novel, can be produced from those 3-aryluracils of formula I' given above in which $R^2$ and $R^3$ have the significances given above with the exception of hydrogen by treating such a 3-aryluracil with a chlorinating or brominating agent. For this purpose there is used as the halogenating agent especially phosphorus pentachloride or phosphorus oxychloride or, respectively, phosphorus pentabromide or phosphoryl bromide. If desired, a mixture of phosphorus pentachloride and phosphorus oxychloride or of phosphorus pentabromide and phosphoryl bromide is used, in which case an excess of phosphorus oxychloride or phosphoryl bromide can serve as the diluent. The chlorination or bromination can be carried out in the presence of an inert diluent, especially an aprotic organic solvent such as an aliphatic or aromatic hydrocarbon, e.g. n-hexane, benzene, toluene or a xylene; a halogenated aliphatic hydrocarbon, e.g. methylene chloride, chloroform, or 1,2-dichloroethane; or a halogenated aromatic hydrocarbon, e.g. chlorobenzene, as well as — especially in the case of phosphorus oxychloride or phosphoryl bromide— in the presence of an organic base such as a tertiary amine, e.g. pyridine or N,N-dimethylaniline. The reaction temperatures generally lie between 0° C. and the reflux temperature of the reaction mixture, preferably between 20° C. and 70° C.

The starting materials of formula IX which are used in process variant (e) are for the most part described in European Patent Publication No. 195,346. Those starting materials IX whose production is not described can be produced analogously to the known starting materials. The reactive derivatives of the benzoic acids IX which can also be used as starting materials can be produced from these benzoic acids according to methods known per se. On the other hand, all enol ethers of the benzoic acids IX, i.e. the compounds of general formulae IXa, as well as their reactive derivatives, which can also be used as starting materials in process variant (e), are novel. The enol ethers can be produced, for example, in accordance with the following Reaction Scheme in which $R^{1'}$, $R^4$, $R^5$, $R^{6'}$, $R^{7'}$ and Hal have the significances given above and $R^{13}$ signifies lower alkyl, preferably $C_{1-4}$-alkyl:

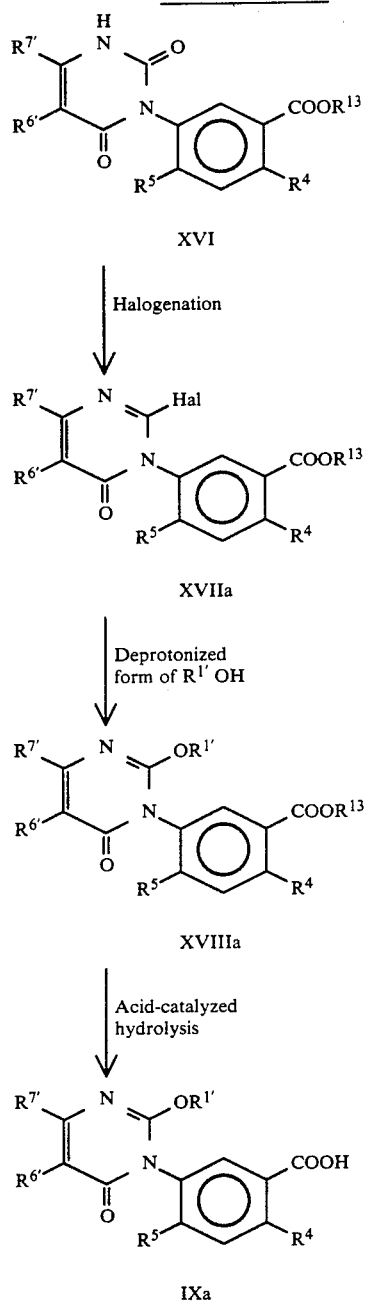

The halogenation of the 3-aryluracil of formula XVI can be carried out analogously to the above-described halogenation of the 3-aryluracil of formula I' to give the starting materials of formula VIIIa and the treatment of the compound of formula XVIIa with the deprotonized form of the hydroxy compound $R^{1'}OH$ can be carried out analogously to process variant (d). The subsequent hydrolysis of the enol ether XVIIIa is conveniently effected in the presence of sulphuric acid as the acidic catalyst, in a chlorinated aliphatic hydrocarbon, preferably methylene chloride, as the solvent and at temperatures between −30° C. and 30° C., preferably between 0° C. and room temperature. Excess sulphuric acid can itself serve as the solvent without an additional solvent.

The reactive derivatives of the enol ethers IXa which can also be used as starting materials can be produced from the enol ethers according to methods known per se.

The compounds of formulae IV, VI and VII, alkylating agents, hydroxy compounds R¹'OH and amines of formula X which are required as starting materials or reagents in process variants (a), (b), (c), (d) and (e) as well as the starting materials of formula XI involved in Reaction Scheme 1 are either known or can be produced according to methods known per se. The starting materials of formula XVI involved in Reaction Scheme 2 are for the most part described in European Patent Publication No. 195,346. Those starting materials XVI whose manufacture is not described can be produced analogously to the known starting materials.

The compounds of formula I, their enol ethers as well as the salts of the compounds I and enol ethers (referred to hereinafter together as compounds in accordance with the invention) possess herbicidal properties and are suitable for the control of weeds, including weed grasses, e.g. Setaria faberii, Digitaria sanguinalis, Poa annua, Chenopodium album, Amaranthus retroflexus, Abutilon theophrasti, Sinapis alba and Datura stramonium, in diverse crop cultivations. Moreover, the compounds are not only pre-emergence herbicides, but also post-emergence herbicides.

In practice, a concentration of 0.001 to 3 kg of compound in accordance with the invention/ha, preferably 10 to 300 g of compound in accordance with the invention/ha, is sufficient to achieve the desired herbicidal effect. The concentration range 15 to 200 g of compound in accordance with the invention/ha is especially preferred.

The weed control composition in accordance with the invention is characterized in that it contains an effective amount of at least one compound in accordance with the invention as well as formulation adjuvants. The composition conveniently contains at least one of the following formulation adjuvants: solid carrier substances; solvents or dispersion media; tensides (wetting and emulsifying agents); dispersing agents (without tenside action); and stabilizers. With the use of these and other adjuvants these compounds, namely the herbicidally active substances, can be converted into the usual formulations such as dusts, powders, granulates, solutions, emulsions, suspensions, emulsifiable concentrates, pastes and the like.

The compounds of formula I as well as their enol ethers are generally insoluble in water, whereas the salts, especially the alkali metal salts and ammonium salts, are generally soluble in water, and can be formulated according to methods which are usual for water-insoluble or water-soluble compounds using the respective formulation adjuvants. The manufacture of the compositions can be carried out in a manner known per se, e.g. by mixing the respective active substance with solid carrier substances, by dissolution or suspension in suitable solvents or dispersion media, if necessary using tensides as wetting or emulsifying agents and/or dispersing agents, by diluting pre-prepared emulsifiable concentrates with solvents or dispersion media etc.

As solid carrier substances there essentially come into consideration: natural mineral substances such as chalk, dolomite, limestone, aluminas and silicic acid and salts thereof (for example siliceous earth, kaolin, bentonite, talc, attapulgite and montmorillonite); synthetic mineral substances such as highly dispersible silicic acid, aluminium oxide and silicates; organic substances such as cellulose, starch, urea and synthetic resins; and fertilizers such as phosphates and nitrates, whereby such carrier substances can be present e.g. as powders or as granulates.

As solvents or dispersion media there essentially come into consideration: aromatics such as benzene, toluene, xylenes and alkylnaphthalenes; chlorinated aromatics and chlorinated aliphatic hydrocarbons such as chlorobenzenes, chloroethylenes and methylene chloride; aliphatic hydrocarbons such as cyclohexane and paraffins, e.g. petroleum fractions; alcohols such as butanol and glycol, as well as their ethers and esters; ketones such as acetone, methyl ethyl ketone, methyl isobutyl ketone and cyclohexanone; and strongly polar solvents or dispersion media such as dimethylformamide, N-methylpyrrolidone and dimethyl sulphoxide, such solvents preferably having flash points of at least 30° C. and boiling points of at least 50° C., and water. Among the solvents or dispersion media there also come into consideration so-called liquified gaseous extenders or carrier substances, which are those products which are gaseous at room temperature and under normal pressure. Examples of such products are especially aerosol propellants such as halogenated hydrocarbons, e.g. dichlorodifluoromethane. If the weed control composition in accordance with the invention is present in the form of a pressurized pack, then a solvent is conveniently used in addition to the propellant.

The tensides (wetting and emulsifying agents) can be non-ionic compounds such as condensation products of fatty acids, fatty alcohols or fatty-substituted phenols with ethylene oxide; fatty acid esters and ethers of sugars or polyvalent alcohols; the products which are obtained from sugars or polyvalent alcohols by condensation with ethylene oxide; block polymers of ethylene oxide and propylene oxide; or alkyldimethylamine oxides.

The tensides can also be anionic compounds such as soaps; fatty sulphate esters, e.g. dodecyl sodium sulphate, octadecyl sodium sulphate and cetyl sodium sulphate; alkyl sulphonates, aryl sulphonates and fatty-aromatic sulphonates such as alkylbenzene sulphonates, e.g. calcium dodecylbenzenesulphonate, and butylnaphthalene sulphonates; and more complex fatty sulphonates, e.g. the amide condensation products of oleic acid and N-methyltaurine and the sodium sulphonate of dioctyl succinate.

Finally, the tensides can be cationic compounds such as alkyldimethylbenzylammonium chlorides, dialkyldimethylammonium chlorides, alkyltrimethylammonium chlorides and ethoxylated quaternary ammonium chlorides.

As dispersing agents (without tenside action) there essentially come into consideration; lignin, sodium and ammonium salts of lignin sulphonic acids, sodium salts of maleic anhydride-diisobutylene copolymers, sodium and ammonium salts of sulphonated polycondensation products of naphthalene and formaldehyde, and sulphite lyes.

As dispersing agents, which are especially suitable as thickening or anti-settling agents, there can be used e.g. methylcellulose, carboxymethylcellulose, hydroxyethylcellulose, polyvinyl alcohol, alginates, caseinates and blood albumin.

Examples of suitable stabilizers are acid-binding agents, e.g. epichlorohydrin, phenyl glycidyl ether and soya epoxides; antioxidants, e.g. gallic acid esters and butylhydroxytoluene; UV-absorbers, e.g. substituted benzophenones, diphenylacrylonitrile acid esters and cinnamic acid esters; and deactivators, e.g. salts of ethylenediaminotetraacetic acid and polyglycols.

The weed control compositions in accordance with the invention can contain, in addition to the active substances in accordance with the invention, synergists and other active substances, e.g. insecticides, acaricides, fungicides, plant growth regulators and fertilizers. Such combination compositions are suitable for intensifying the activity or for broadening the spectrum of activity.

The weed control compositions in accordance with the invention generally contain between 0.001 and 95 weight percent, preferably between 0.5 and 75 weight percent, of one or more compounds in accordance with the invention as the active substance(s). They can be present e.g. in a form which is suitable for storage and transport. In such formulations, e.g. emulsifiable concentrates, the active substance concentration is normally in the higher range, preferably between 1 and 50 weight percent, especially between 10 and 30 weight percent. These formulations can then be diluted, e.g. with the same or different inert substances, to give active substance concentrations which are suitable for practical use, i.e. preferably about 0.001 to 10 weight percent, especially about 0.005 to 5 weight percent. The active substance concentrations can, however, also be smaller or greater.

As mentioned above, the manufacture of the weed control compositions in accordance with the invention can be carried out in a manner known per se.

For the manufacture of pulverous preparations the active substance, i.e. at least one compound in accordance with the invention, can be mixed with a solid carrier substance, e.g. by grinding together; or the solid carrier substance can be impregnated with a solution or suspension of the active substance and then the solvent or dispersion medium can be removed by evaporation, heating or sucking-off under reduced pressure. By adding tensides or dispersing agents such pulverous preparations can be made readily wettable with water, so that they can be converted into aqueous suspensions which are suitable e.g. as spray compositions.

The active substance can also be mixed with a tenside and a solid carrier substance to form a wettable powder which is dispersible in water, or it can be mixed with a solid pre-granulated carrier substance to form a product in the form of a granulate.

When desired, the active substance can be dissolved in a water-immiscible solvent such as, for example, a high-boiling hydrocarbon, which conveniently contains dissolved emulsifying agent, so that the solution becomes self-emulsifying upon addition to water. Alternatively, the active substance can be mixed with an emulsifying agent and the mixture can then be diluted with water to the desired concentration. Moreover, the active substance can be dissolved in a solvent and thereafter the solution can be mixed with an emulsifying agent. Such a mixture can likewise be diluted with water to the desired concentration. In this manner there are obtained emulsifiable concentrates or ready-for-use emulsions.

The use of the weed control compositions in accordance with the invention, which forms a further object of the present invention, can be carried out according to usual application methods such as sprinkling, spraying, dusting, watering or scattering. The method in accordance with the invention for the control of weeds is characterized by treating the locus to be protected against weeds and/or the weeds with a compound in accordance with the invention or with a weed control composition in accordance with the invention.

The following Examples serve to illustrate the invention in more detail.

I. MANUFACTURE OF THE COMPOUNDS OF FORMULA I

EXAMPLE 1

4.4 g of a 55% dispersion of sodium hydride in oil are suspended in 110 ml of dimethylformamide and a solution of 18.2 g of ethyl 4,4,4-trifluoro-3-aminocrotonate in 10 ml of dimethylformamide is added dropwise to the suspension at 10° C. After completion of the hydrogen evolution 30.5 g of ethyl 4-chloro-2-fluoro-5-(N-methoxy-N-methylcarbamoyl)-carbanilate are added dropwise and the reaction mixture is stirred at 150° C. for 1 hour while continuously distilling off the ethanol formed in the reaction.

The mixture is subsequently poured on to 200 ml of ice-water, the aqueous mixture is acidified to pH 3 with 2N hydrochloric acid, the aqueous phase is extracted three times with 150 ml of ethyl acetate each time, the combined organic extracts are washed to neutrality, and the organic phase is dried over anhydrous sodium sulphate and evaporated. The oily product is treated with active charcoal and thereafter crystallized from diethyl ether. There is obtained N-methoxy-N-methyl-2-chloro-5-[3,6-dihydro-2,6-dioxo-4-trifluoromethyl-1(2H)-pyrimidinyl]-4-fluorobenzamide, m.p. above 220° C.;

|  | C % | H % | N % | Cl % | F % |
|---|---|---|---|---|---|
| Calculated | 42.50 | 2.55 | 10.62 | 8.96 | 19.20 |
| Found | 42.91 | 2.75 | 10.42 | 8.79 | 18.85 |

EXAMPLE 2

Analogously to the procedure described in Example 1, starting from ethyl 4,4,4-trifluoro-3-aminocrotonate and ethyl 4-chloro-2-fluoro-5-(N-isopropylcarbamoyl)-carbanilate there is obtained N-isopropyl-2-chloro-5-[3,6-dihydro-2,6-dioxo-4-trifluoromethyl-1(2H)-pyrimidinyl]-4-fluorobenzamide, m.p. 234°–239° C.

EXAMPLE 3

An 80% suspension of 1.75 g of sodium hydride in refined oil is placed in 20 ml of dimethylformamide and 2.5 ml of toluene. 10.2 g of ethyl 4,4,4-trifluoro-3-aminocrotonate in 50 ml of dimethylformamide are added dropwise to the mixture at 5° to 15° C. and the thus-obtained reaction solution is stirred for 1 hour and subsequently cooled to −50° to −60° C. 12.6 g of N,N-diethyl-2-chloro-4-fluoro-5-isocyanatobenzamide in 25 ml of toluene are then added dropwise thereto and the mixture is stirred at this low temperature for a further 2 hours. Thereafter, the reaction solution is left to stand for about 16 hours, whereby it warms to room temperature. The solution is poured into 1 l of water and the aqueous solution is adjusted to a pH value of 5 with the addition of glacial acetic acid. Subsequently, the solution is extracted twice with 1 l of acetic acid, washed once with 1 l of water and once with 500 ml of saturated sodium chloride solution. The organic phases are combined, dried with anhydrous magnesium sulphate and concentrated. The residue obtained is recrystallized from ethyl acetate. In this manner there is obtained N,N-diethyl-2-chloro-5-[3,6-dihydro-2,6-dioxo-4-trifluoromethyl-1(2H)-pyrimidinyl]-4-fluorobenzamide, m.p. 253°–254° C.

EXAMPLE 4

A mixture of 19.8 g of N-methoxy-N-methyl-2-chloro-5-[3,6-dihydro-2,6-dioxo-4-trifluoromethyl-1(2H)-pyrimidinyl]-4-fluorobenzamide, 5.7 ml of dimethyl sulphate as well as 14.0 g of sodium carbonate in 80 ml of acetonitrile is stirred at 50° C. for 1 hour. The mixture is then treated with 150 ml of ice-water and the aqueous mixture is extracted three times with 150 ml of ethyl acetate each time. The combined organic phases are washed to neutrality, dried over anhydrous sodium sulphate and the solvent is evaporated. The crude product is recrystallized from diethyl ether/n-hexane and gives N-methoxy-N-methyl-2-chloro-5-[3,6-dihydro-2,6-dioxo-3-methyl-4-trifluoromethyl-1(2H)-pyrimidinyl]-4-fluorobenzamide, m.p. 158° C.

EXAMPLES 5 AND 6

Analogously to the procedure described in Example 4, starting from corresponding N-monosubstituted or N,N-disubstituted 2-chloro-5-[3,6-dihydro-2,6-dioxo-4-trifluoromethyl-1(2H)-pyrimidinyl]-4-fluorobenzamide by alkylation with the corresponding dialkyl sulphate there are obtained the compounds of formula I set forth in Table 1 hereinafter:

TABLE 1

| Example | $R^1$ | $NR^2R^3$ | Physical data |
|---|---|---|---|
| 5 | $CH_3$ | $N(C_2H_5)_2$ | M.p. 144–148° C. |
| 6 | $C_2H_5$ | $NH[CH(CH_3)_2]$ | M.p. 165–166° C. |

EXAMPLE 7

A solution of 0.54 g of sodium methylate in 5 ml of methanol is added dropwise to a suspension of 4.14 g of N-methoxy-N-methyl-2-chloro-5-[2-chloro-4-oxo-6-trifluoromethyl-3(4H)-pyrimidinyl]-4-fluorobenzamide in 25 ml of methanol and the reaction mixture is stirred for 10 minutes. The mixture is then treated with 30 ml of ethyl acetate as well as 50 ml of n-hexane, filtered and the filtrate is evaporated. The resulting colourless, viscous crude product crystallizes from diethyl ether/n-hexane. There is obtained N-methoxy-N-methyl-2-chloro-4-fluoro-5-[2-methoxy-4-oxo-6-trifluoromethyl-3(4H)-pyrimidinyl]-benzamide, m.p. 119° C.

EXAMPLE 8

A mixture of 3.5 g of 2-chloro-5-[3,6-dihydro-2,6-dioxo-3-methyl-4-trifluoromethyl-1(2H)-pyrimidinyl]-4-fluorobenzoic acid and 3.4 ml of thionyl chloride in 20 ml of benzene is heated to reflux temperature for 3 hours together with 2 drops of dimethylformamide. The mixture is then evaporated to dryness and the residue is dissolved in 15 ml of dioxan. The solution is added dropwise at room temperature to a solution of 0.7 g of isopropylamine and 1.1 g of pyridine in 15 ml of dioxan and the reaction mixture is stirred at room temperature for 2.5 hours. Subsequently, the mixture is treated with 400 ml of water, extracted twice with 400 ml of ethyl acetate each time, the organic phases are washed twice with 200 ml of 1N hydrochloric acid each time, thereafter twice with 200 ml of saturated sodium chloride solution each time, and the combined organic phases are dried over anhydrous sodium sulphate and evaporated. The residue is purified by chromatography on silica gel with ethyl acetate/n-hexane (1:2) as the eluent. In this manner there is obtained N-isopropyl-2-chloro-5-[3,6-dihydro-2,6-dioxo-3-methyl-4-trifluoromethyl-1(2H)-pyrimidinyl]-4-fluorobenzamide which can be recrystallized from ethyl acetate/n-hexane. M.p. 146°–149° C.

EXAMPLES 9–45

Analogously to the procedure described in Example 8, starting from 2-chloro-5-[3,6-dihydro-2,6-dioxo-3-methyl-4-trifluoromethyl-1(2H)-pyrimidinyl]-4-fluorobenzoic acid there are obtained via its acid chloride by amidation with the corresponding amine $HNR^2R^3$ the compounds of formula I set forth in Table 2 hereinafter:

TABLE 2

| Example | $-NR^2R^3$ | Physical data |
|---|---|---|
| 9 | $NH_2$ | M.p. 188–190° C. |
| 10 | $N(CH_3)_2$ | M.p. 200–203° C. |
| 11 | NH-cyclopropyl | M.p. 188–189° C. |
| 12 | NH-cyclohexyl | Oil; $^1$H-NMR (D$_6$-DMSO, 400 MHz): 1.10–1.35 ppm (m,5H), 1.54–1.60 ppm (m,1H), 1.68–1.73 ppm (m,2H), 1.79–1.84 ppm (m,2H), 3.41 ppm (s,3H), 3.63–3.74 ppm (m,1H), 6.58 ppm (s,1H), 7.55 ppm (d,1H), 7.74 ppm (d,1H), 8.52 ppm (d,1H). |

TABLE 2-continued

Structure: 1-methyl-6-trifluoromethyl-3-(4-fluoro-2-chloro-5-(CONR²R³)phenyl)-2,4(1H,3H)-pyrimidinedione

| Example | —NR²R³ | Physical data |
|---|---|---|
| 13 | NH(CH₂CH=CH₂) | M.p. 127–129° C. |
| 14 | N(CH₃)(CH₂CH=CH₂) | Oil; microanalysis: C% H% N% Calculated 48.64 3.36 10.01 Found 48.71 3.36 9.78 |
| 15 | NH(CH₂C≡CH) | Oil; $^1$H-NMR (D$_6$-DMSO, 400 MHz): 3.15 ppm (t,1H), 3.4 ppm (s,3H), 4.02 ppm (dd,2H), 6.59 ppm (s,1H), 7.60 ppm (d,1H), 7.78 ppm (d,1H), 9.11 ppm (t,1H) |
| 16 | NH(C₆H₅) | M.p. 205–206° C. |
| 17 | NH(CH₂C₆H₅) | M.p. 181–183° C. |
| 18 | NH(CH₂CH₂OH) | M.p. 165–168° C. |
| 19 | NH(CH₂COOC₂H₅) | Oil; $^1$H-NMR (D$_6$-DMSO, 400 MHz): 1.21 ppm (t,3H), 3.42 ppm (s,3H), 3.98 ppm (d,2H), 4.13 ppm (q,2H), 6.60 ppm (s,1H), 7.62 ppm (d,1H), 7.79 ppm (d,1H), 9.07 ppm (t,1H). |
| 20 | NH[C(CH₃)₂(CN)] | M.p. 215–218° C. |
| 21 | pyrrolidin-1-yl | M.p. 209–211° C. |
| 22 | piperidin-1-yl | M.p. 150–152° C. |
| 23 | cis-2,6-dimethylmorpholin-4-yl | Oil; microanalysis: C% H% N% Calculated 49.2 3.91 9.06 Found 49.28 4.29 8.56 |
| 24 | N(CH₃)(OCH₃) | M.p. 158° C. microanalysis: C% H% N% Cl% F% Calculated 43.97 2.95 10.26 8.65 18.55 Found 43.89 3.08 10.18 8.61 18.87 |
| 25 | N(CH₂CH=CH₂)₂ | M.p. 101–102° C. |
| 26 | thiomorpholin-4-yl | M.p. 161–162° C. |
| 27 | NH-(2,4-dichlorophenyl) | M.p. 157–158° C. |
| 28 | NH-(benzo[1,3]dioxol-5-yl) | M.p. 172–173° C. |

TABLE 2-continued

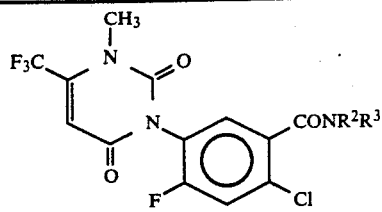

| Example | —NR²R³ | Physical data |
|---|---|---|
| 29 | NH—(3,5-bis-CF₃-phenyl) | M.p. 189–190° C. |
| 30 | NH—CH(CH₃)—phenyl (R-Form) | $[\alpha]_D^{25}$ = +24.25° C.; ¹H-NMR (D₆-DMSO, 400 MHz): 1.42 ppm (d,3H), 3.41 ppm (s,3H), 5.10 ppm (quintet,1H), 6.59 ppm (s,1H), 7.20–7.26 ppm (m,1H), 7.30–7.36 ppm (m,2H), 7.38–7.42 ppm (m,2H), 7.58 ppm (dd,1H), 7.77 ppm (d,1H), 9.14 ppm (d,1H). |
| 31 | NH—(2,4,6-trifluorophenyl) | M.p. 202–204° C. |
| 32 | NH(CH₂CF₃) | M.p. 137–139° C. |
| 33 | NH—CH₂—(4-NO₂-phenyl) | M.p. 234–235° C. |
| 34 | NH—(4-OCF₃-phenyl) | ¹H-NMR (D₆-DMSO, 400 MHz): 3.44 ppm (s,3H), 6.61 ppm (s,1H), 7.38 ppm (d,2H), 7.78 ppm (d,1H), 7.81 ppm (d,2H), 7.88 ppm (d,1H), 10.91 ppm (s,1H). |
| 35 | N(CH₃)(3-CH₃-phenyl) | M.p. 137–139° C. |
| 36 | NH—(2-Cl-4-F-5-COOCH(CH₃)₂-phenyl) | M.p. 180–181° C. |
| 37 | NH—C(CH₃(CN)[CH(CH₃)₂] | M.p. 225–227° C. |
| 38 | NH—C(CH₃)₂C≡CH | ¹H-NMR (D₆-DMSO, 400 MHz): 1.56 ppm (s,6H), 3.15 ppm (s,1H), 3.41 ppm (s,3H), 6.58 ppm (s,1H), 7.56 ppm (d,1H), 7.74 ppm (d,1H), 8.77 ppm (s,1H). |
| 39 | NH[CH₂C(CH₃)=CH₂] | ¹H-NMR (D₆-DMSO, 400 MHz): 1.73 ppm (s,3H), 3.42 ppm (s,3H), 3.77 ppm (d,2H), 4.81 ppm (s,1H), 4.91 ppm (s,1H), 6.60 ppm (s,1H), 7.61 ppm (d,1H), 7.77 ppm (d,1H), 8.84 ppm (t,1H). |
| 40 | NH(C₃H₇n) | M.p. 146–148° C. |
| 41 | NH(C₄H₉n) | M.p. 146–148° C. |

TABLE 2-continued

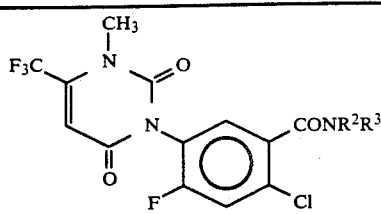

| Example | —NR²R³ | Physical data |
|---|---|---|
| 42 | NH[CH(CH₃)(C₂H₅)] | ¹H-NMR (D₆-DMSO, 400 MHz): 0.90 ppm (t,3H), 1.10 ppm (d,3H), 1.47 ppm (quintet,2H), 3.42 ppm (s,3H), 3.81–3.89 ppm (m,1H), 3.59 ppm (s,1H), 7.55 ppm (d,1H), 7.75 ppm (d,1H), 8.34 ppm (d,1H). |
| 43 | NH(C₂H₅) | M.p. 168–169° C. |
| 44 | NH(C₆H₁₃n) | M.p. 101–103° C. |
| 45 | NH(C₈H₁₇n) | M.p. 85–86° C. |

EXAMPLES 46–54

Analogously to the procedure described in Example 8, starting from the corresponding 2-chloro-5-[3,6-dihydro-2,6-dioxo-1(2H)-pyrimidinyl]-benzoic acid there are obtained via its acid chloride by amidation with the corresponding amine HNR²R³ the compounds of formula I set forth in Table 3 hereinafter:

TABLE 3

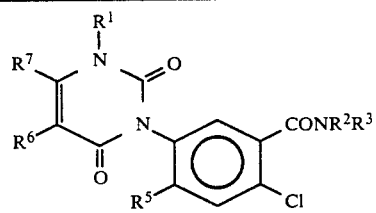

| Example | R¹ | R⁵ | R⁶ | R⁷ | NR²R³ | Physical data |
|---|---|---|---|---|---|---|
| 46 | CH₃ | F | \<cyclopentyl ring across R⁶–R⁷\> | | | N(CH₃)(OCH₃) | M.p. 105° C. | microanalysis:
Calculated:
C %   H %   N %   Cl %   F %
53.48   4.49   11.00   9.28   4.98
Found:
C %   H %   N %   Cl %   F %
53.34   4.62   10.70   9.24   4.98

| Example | R¹ | R⁵ | R⁶ | R⁷ | NR²R³ | Physical data |
|---|---|---|---|---|---|---|
| 47 | CH₃ | F | H | CH₃ | NH(CH₂CH=CH₂) | M.p. 202–203° C. |
| 48 | CH₃ | F | H | CH₃ | NH[C(CH₃)₂(CN)] | M.p. 217–218° C. |
| 49 | CH₃ | H | \<cyclopentyl\> | | | N(C₂H₅)₂ | M.p. 142–146° C. |
| 50 | CH₃ | H | \<cyclopentyl\> | | | NHC₆H₅ | M.p. 245–249° C. |
| 51 | CH₃ | H | \<cyclopentyl\> | | | NHCH₃ | M.p. 195–199° C. |
| 52 | CH₃ | F | H | C₂F₅ | NH(CH₂CH=CH₂) | M.p. 133–134° C. |
| 53 | CHF₂ | F | H | CH₃ | NH(CH₂CH=CH₂) | M.p. 154–156° C. |
| 54 | CH₃ | H | H | CF₃ | NH(CH₂CH=CH₂) | M.p. 141–142° C. |

EXAMPLES 55-58

Analogously to the procedure described in Example 8, starting from the corresponding 5-[2-methoxy-6-oxo-4-trifluoromethyl-1(6H)-pyrimidinyl]-benzoic acid there are obtained by amidation with the corresponding amine HNR$^2$R$^3$ the enol ethers of formula Ia set forth in Table 4 hereinafter:

TABLE 4

[Structure: F$_3$C-C=N-C(OCH$_3$)=... with N-CH$_2$-C(=O)-R$^5$ attached to benzene ring bearing COOH and Cl]

| Example | R$^5$ | NR$^2$R$^3$ | Physical data |
|---------|-------|-------------|---------------|
| 55 | F | NH(CH$_2$CH=CH$_2$) | M.p. 147-148° C. |
| 56 | F | NH[C(CH$_3$)$_2$(CN)] | M.p. 200-201° C. |
| 57 | F | N(C$_2$H$_5$)$_2$ | $^1$H-NMR(CDCl$_3$, 400 MHz): 1.10 ppm (t, 3H), 1.26 ppm(t,3H), 3.15-3.25 ppm(m,2H), 3.30-3.80 ppm(m,2H), 4.00 ppm (s,3H), 6.59 ppm (s,1H), 7.19 ppm (d,1H), 7.35 ppm (d,1H) |
| 58 | H | NH(CH$_2$CH=CH$_2$) | M.p. 62-63° C. |

II. PRODUCTION OF THE STARTING MATERIALS OF FORMULAE II, III, XIII AND XIV

EXAMPLE 59

A mixture of 329 g of 2-chloro-4-fluoro-5-nitrobenzoic acid and 350 ml of thionyl chloride is stirred at 60° C. for 1.5 hours. Subsequently, the excess thionyl chloride is distilled off and the oily residue is distilled at 120° C. and 0.05 mmHg. The collected liquid product crystallizes upon cooling. There is thus obtained 2-chloro-4-fluoro-5-nitrobenzoyl chloride, m.p. 51° C.

119 g of the above product and 58.5 g of N,O-dimethylhydroxylamine hydrochloride are placed in 750 ml of tetrahydrofuran and the resulting suspension is cooled to 0° C. 165 ml of triethylamine are added dropwise within 40 minutes while stirring vigorously and the reaction mixture is stirred at 0° C. for 1 hour. The mixture is subsequently poured into 1 liter of water, the aqueous phase is extracted three times with 250 ml of ethyl acetate each time, the combined organic phases are washed to neutrality, dried over anhydrous sodium sulphate and the solvent is distilled off. The oily residue is then purified by chromatography on 1 kg of silica gel with n-hexane/ethyl acetate (7:3) as the eluent and the product is recrystallized from diethyl ether/n-hexane. In this manner there is obtained N-methoxy-N-methyl-2-chloro-4-fluoro-5-nitrobenzamide, m.p. 89° C.

EXAMPLES 60 AND 61

Analogously to the procedure described in the second part of Example 59, starting from 2-chloro-4-fluoro-5-nitrobenzamide and the corresponding amine HNR$^2$R$^3$ there are obtained the N-monosubstituted or N,N-di-substituted 2-chloro-4-fluoro-5-nitro-benzamide of formula XIII set forth in Table 5 hereinafter:

TABLE 2

[Structure: benzene ring with O$_2$N, CONR$^2$R$^3$, F, Cl substituents]

| Example | NR$^2$R$^3$ | Physical data |
|---------|-------------|---------------|
| 60 | NH[CH(CH$_3$)$_2$] | M.p. 158-160° C. |
| 61 | N(C$_2$H$_5$)$_2$ | M.p. 82-83° C. |

EXAMPLE 62

A suspension of 140 g of iron powder in a mixture of 400 ml of ethanol, 60 ml of water and 4.5 ml of 32% hydrochloric acid is heated to 70° C. by means of an oil bath while stirring. After removing the oil bath 105 g of N-methoxy-N-methyl-2-chloro-4-fluoro-5-nitrobenzamide are added portionwise within 45 minutes in such a manner that the reaction solution boils gently. Subsequently, 4 g of active charcoal are added and the mixture is stirred at boiling temperature for a further 5 minutes. The mixture is cooled and neutralized with 2 g of sodium carbonate. The mixture is then filtered through 50 g of Celite and the filtrate is concentrated. The product crystallizes out and is thereafter filtered off under suction, washed with 100 ml of n-hexane and dried. There is obtained N-methoxy-N-methyl-5-amino-2-chloro-4-fluorobenzamide, m.p. 118° C.

EXAMPLES 63 AND 64

Analogously to the procedure described in Example 62, starting from the corresponding N-monosubstituted or disubstituted 2-chloro-4-fluoro-5-nitrobenzamide by reduction using iron powder there is obtained the N-monosubstituted or N,N-disubstituted 5-amino-2-chloro-4-fluorobenzamide of formula XIV set forth in Table 6 hereinafter:

TABLE 6

[Structure: benzene ring with H$_2$N, CONR$^2$R$^3$, F, Cl substituents]

| Example | NR$^2$R$^3$ | Physical data |
|---------|-------------|---------------|
| 63 | NH[CH(CH$_3$)$_2$] | M.p. 113-115° C. |
| 64 | N(C$_2$H$_5$)$_2$ | M.p. 105-106° C. |

EXAMPLE 65

55.6 g of N-methoxy-N-methyl-5-amino-2-chloro-4-fluorobenzamide are dissolved in 200 ml of pyridine and the solution is cooled to 0° C. 30.4 g of ethyl chloroformate are added dropwise at 0° C. while stirring and thereafter the reaction mixture is stirred for 14 hours. The mixture is poured into 1 liter of ice-water, the aqueous mixture is extracted three times with 250 ml of ethyl acetate each time, the combined organic phases are washed to neutrality, dried over anhydrous sodium sulphate and the solvent is evaporated off. The product is crystallized from diethyl ether. In this manner there is obtained ethyl 4-chloro-2-fluoro-5-(N-methoxy-N-methylcarbamoyl)-carbanilate, m.p. 121° C., used as the starting material in Example 1.

EXAMPLE 66

Analogously to the procedure described in Example 65, starting from N-isopropyl-5-amino-2-chloro-4-fluorobenzamide and ethyl chloroformate there is obtained ethyl 4-chloro-2-fluoro-5-(N-isopropylcarbamoyl)-carbanilate, m.p. 127°–130° C., used as the starting material in Example 2.

EXAMPLE 67

13.5 g of of N,N-diethyl-5-amino-2-chloro-4-fluorobenzamide in 150 ml of ethyl acetate are added dropwise while stirring within 30 minutes to a solution, heated to 70° C., of 6.7 ml of diphosgene in 50 ml of ethyl acetate. The reaction mixture is then heated at reflux temperature for 2 hours. Subsequently, the solvent is distilled off at normal pressure and the residue is distilled in a bulb-tube. There is obtained N,N-diethyl-2-chloro-4-fluoro-5-isocyanatobenzamide, b.p. 170° C./0.06 mmHg; $n_D$ 1.542, used as the starting material in Example 3.

III. PRODUCTION OF THE STARTING MATERIALS OF FORMULAE VIIIa, IX AND IXa

EXAMPLE 68

The N-methoxy-N-methyl-2-chloro-5-[2-chloro-4-oxo-6-trifluoromethyl-3(4H)-pyrimidinyl]-4-fluorobenzamide used in Example 7 can be produced as follows:

A mixture of 1.98 g of N-methoxy-N-methyl-2-chloro-5-[3,6-dihydro-2,6-dioxo-4-trifluoromethyl-1(2H)-pyrimidinyl]-4-fluorobenzamide, 1.5 ml of phosphorus oxychloride and 1.2 ml of pyridine in 10 ml of toluene is stirred at 80° C. for 3.5 hours. The mixture is then treated with 50 ml of ice-water and extracted three times with 80 ml of ethyl acetate each time. The combined organic phases are washed to neutrality, dried over anhydrous sodium sulphate and treated with 200 ml of n-hexane, and the mixture is filtered through 20 g of silica gel. The mixture is then concentrated and the product is left to crystallize out. In this manner there is obtained N-methoxy-N-methyl-2-chloro-5-[2-chloro-4-oxo-6-trifluoromethyl-3(4H)-pyrimidinyl]-4-fluorobenzamide, m.p. 183° C.;

|  | C % | H % | N % | Cl % | F % |
|---|---|---|---|---|---|
| Calculated | 40.60 | 2.19 | 10.15 | 17.12 | 18.35 |
| Found | 40.72 | 2.29 | 10.07 | 17.11 | 18.42 |

EXAMPLE 69

The 2-chloro-5-[3,6-dihydro-2,6-dioxo-3,4-dimethyl-1(2H)-pyrimidinyl]-4-fluorobenzoic acid used as the starting material in Examples 47 and 48 can be produced as follows:

A mixture of 35 g of isopropyl 2-chloro-5-[3,6-dihydro-2,6-dioxo-3,4-dimethyl-1(2H)-pyrimidinyl]-4-fluorobenzoate, 165 ml of concentrated sulphuric acid and 165 ml of methylene chloride is stirred well at room temperature for 30 minutes. Subsequently, the reaction mixture is poured cautiously onto 500 g of ice. The aqueous mixture is extracted twice with 250 ml of ethyl acetate each time and the organic phase is extracted three times with 200 ml of saturated sodium bicarbonate solution each time. The aqueous sodium bicarbonate solutions are combined and acidified with concentrated sulphuric acid. The separated product is extracted twice with 600 ml of ethyl acetate each time and the organic phases are washed twice with 200 ml of water each time, dried over anhydrous magnesium sulphate and concentrated. In this manner there is obtained 2-chloro-5-[3,6-dihydro-2,6-dioxo-3,4-dimethyl-1(2H)-pyrimidinyl]-4-fluorobenzoic acid which can be purified further by digestion in ethanol. M.p. 236°–239° C.

EXAMPLES 70–73

Analogously to the procedure described in Example 69, starting from the corresponding isopropyl 2-chloro-5-[3,6-dihydro-2,6-dioxo-1(2H)-pyrimidinyl]-4-fluorobenzoate there are obtained by acid-catalyzed hydrolysis the starting materials (benzoic acids) of formula IX set forth in Table 7 hereinafter:

TABLE 7

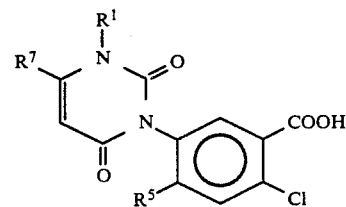

| Example | Example No. of the end product I | $R^1$ | $R^5$ | $R^7$ | Physical Data |
|---|---|---|---|---|---|
| 70 | 8–45 | $CH_3$ | F | $CF_3$ | M.p. 239–242° C. |
| 71 | 52. | $CH_3$ | F | $C_2F_5$ | M.p. 229–231° C. |
| 72 | 53 | $CHF_2$ | F | $CH_3$ | M.p. 247–248° C. |
| 73 | 54 | $CH_3$ | H | $CF_3$ | M.p. 235–236° C. |

EXAMPLES 74 AND 75

Analogously to the procedure described in Example 69, starting from the corresponding isopropyl 5-[2-methoxy-6-oxo-4-trifluoromethyl-1(6H)-pyrimidinyl]-benzoate there are obtained by acid-catalyzed hydrolysis the starting materials (benzoic acids) of formula IXa set forth in Table 8 hereinafter:

TABLE 8

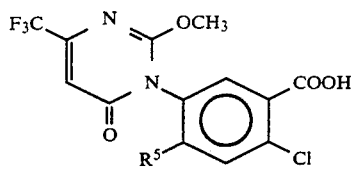

| Example | Example No. of the end product Ia | $R^5$ | Physical data |
|---|---|---|---|
| 74 | 55–57 | F | M.p. 205–210° C. |
| 75 | 58 | H | M.p. 265–268° C. |

IV. FORMULATION EXAMPLES

EXAMPLE 76

An emulsifiable concentrate contains the following ingredients:

| Compound in accordance with the invention (active substance) | 250 g/l |
|---|---|
| Polyaryl polyethoxylate (emulsifier) | 300 g/l |
| N-Methylpyrrolidone (solvent) | ad 1000 ml |

The active substance and the emulsifier are dissolved in the solvent while stirring and the solution is made up to 1 liter with further solvent.

The resulting emulsifiable concentrate can be emulsified in water and then gives a ready-for-use spray liquor having the desired concentration.

EXAMPLE 77

For the manufacture of a 25% spray powder the ingredients listed hereinafter are mixed with one another:

| | |
|---|---|
| Compound in accordance with the invention (active substance) | 25 g |
| Silicic acid, hydrated (carrier material, milling aid) | 5 g |
| Sodium lauryl sulphate (wetting agent) | 1 g |
| Sodium lignosulphonate (dispersing agent) | 2 g |
| Kaolin (carrier material) | 67 g |
| | 100 g |

Subsequently, the mixture is finely milled using a pinned disc mill or comparable milling aggregate.

Upon stirring in water the resulting spray powder gives a fine suspension which is suitable as a ready-for-use spray liquor.

We claim:

1. Compounds of the formula

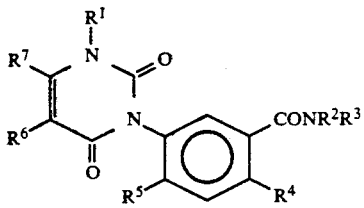

wherein $R^1$ signifies hydrogen, $C_{1-4}$-alkyl, $C_{1-4}$-haloalkyl, $C_3$ or 4-alkenyl or $C_3$ or 4-alkynyl, $R^2$ and $R^3$ each independently signify hydrogen, $C_{1-8}$-alkyl, $C_{2-8}$-alkenyl, $C_{3-8}$-alkynyl, $C_{1-8}$-haloalkyl, $C_{1-8}$-hydroxyalkyl, $C_{1-4}$-alkoxy-$C_{1-8}$-alkyl, $C_{1-4}$-alkylthio-$C_{1-8}$-alkyl, $C_{1-4}$-haloalkoxy-$C_{1-8}$-alkyl, $C_{2-8}$-cyanoalkyl, $C_{1-8}$-nitroalkyl, $C_{2-9}$-carboxyalkyl, $C_{2-5}$-alkoxycarbonyl-$C_{1-8}$-alkyl, $C_{1-4}$-alkylsulphonyl-$C_{1-8}$-alkyl, di($C_{1-4}$-alkyl)-phosphono-$C_{1-8}$-alkyl, $C_{3-8}$-cycloalkyl, $C_{1-8}$-alkoxy or phenyl or phenyl-$C_{1-4}$-alkyl optionally substituted with halogen, hydroxy, $C_{1-4}$-alkyl, $C_{1-4}$-haloalkyl, $C_{1-4}$-alkoxy, $C_{1-4}$-alkylthio, $C_{1-4}$-haloalkoxy, cyano, nitro, carboxy and/or $C_{2-5}$-alkoxycarbonyl, whereby this optionally substituted phenyl can have a fused, saturated, carbocyclic five- to seven-membered ring or a fused, saturated, heterocyclic five- to seven-membered ring containing 1 or 2 oxygen atoms, whereby $R^2$ and $R^3$ cannot both stand for $C_{1-8}$-alkoxy, $R^2$ and $R^3$ together with the nitrogen atom to which they are attached signify a four- to seven-membered heterocyclic ring which is optionally mono- or multiply substituted with $C_{1-6}$-alkyl and which, in addition to the nitrogen atom, can also have in the ring an oxygen atom, a sulphur atom and/or a second nitrogen atom, $R^4$ signifies halogen or cyano, $R^5$ signifies hydrogen or halogen, $R^6$ signifies hydrogen, halogen or $C_{1-4}$-alkyl, $R^7$ signifies $C_{1-4}$-alkyl or, where $R^1$ is different from $C_{1-4}$-haloalkyl, also $C_{1-4}$-haloalkyl, or $R^6$ and $R^7$ together signify tri- or tetramethylene, and the corresponding enol ethers of those compounds of formula I in which $R^1$ signifies $C_{1-4}$-alkyl, $C_3$ or 4-alkenyl or $C_3$ or 4-alkynyl, $R^6$ signifies hydrogen, halogen or $C_{1-4}$-alkyl and $R^7$ signifies $C_{1-4}$-haloalkyl, as well as salts of those compounds of formula I or enol ethers in which $R^1$ and/or $R^2$ signify hydrogen.

2. Compounds according to claim 1, wherein $R^1$ signifies $C_{1-4}$-alkyl or $C_{1-4}$-fluoroalkyl.

3. Compounds according to claim 1, wherein $R^2$ signifies hydrogen or $C_{1-8}$-alkyl and $R^3$ signifies $C_{1-8}$-alkyl, $C_{2-8}$-alkenyl, $C_{3-8}$-alkynyl, $C_{2-8}$-cyanoalkyl or $C_{3-8}$-cycloalkyl.

4. Compounds according to claim 1, wherein $R^2$ signifies hydrogen or $C_{1-8}$-alkyl and $R^3$ signifies benzyl.

5. Compounds according to claim 1, wherein $R^4$ signifies chlorine or bromine and $R^5$ signifies hydrogen or fluorine.

6. Compounds according to claim 1, wherein $R^6$ signifies hydrogen, fluorine or methyl and $R^7$ signifies $C_{1-4}$-haloalkyl.

7. Compounds according to claim 1, wherein $R^6$ signifies hydrogen, fluorine or methyl and $R^7$ signifies $C_{1-4}$-alkyl.

8. A compound according to claim 1, selected from
N-ethyl-2-chloro-5-[3,6-dihydro-2,6-dioxo-3-methyl-4-trifluoromethyl-1(2H)-pyrimidinyl]-4-fluorobenzamide,
N-propyl-2-chloro-5-[3,6-dihydro-2,6-dioxo-3-methyl-4-trifluoromethyl-1(2H)-pyrimidinyl]-4-fluorobenzamide,
N-isopropyl-2-chloro-5-[3,6-dihydro-2,6-dioxo-3-methyl-4-trifluoromethyl-1(2H)-pyrimidinyl]-4-fluorobenzamide,
N-butyl-2-chloro-5-[3,6-dihydro-2,6-dioxo-3-methyl-4-trifluoromethyl-1(2H)-pyrimidinyl]-4-fluorobenzamide,
N-(sec.butyl)-2-chloro-5-[3,6-dihydro-2,6-dioxo-3-methyl-4-trifluoromethyl-1(2H)-pyrimidinyl]-4-fluorobenzamide,
N-allyl-2-chloro-5-[3,6-dihydro-2,6-dioxo-3-methyl-4-trifluoromethyl-1(2H)-pyrimidinyl]-4-fluorobenzamide,
N-(2-methyl-2-propenyl)-2-chloro-5-[3,6-dihydro-2,6-dioxo-3-methyl-4-trifluoromethyl-1(2H)-pyrimidinyl]-4-fluorobenzamide,
N-propargyl-2-chloro-5-[3,6-dihydro-2,6-dioxo-3-methyl-4-trifluoromethyl-1(2H)-pyrimidinyl]-4-fluorobenzamide,
N-(1,1-dimethyl-2-propynyl)-2-chloro-5-[3,6-dihydro-2,6-dioxo-3-methyl-4-trifluoromethyl-1(2H)-pyrimidinyl]-4-fluorobenzamide,
N-(1-cyano-1-methylethyl)-2-chloro-5-[3,6-dihydro-2,6-dioxo-3-methyl-4-trifluoromethyl-1(2H)-pyrimidinyl]-4-fluorobenzamide,
N-(1-cyano-1,2-dimethylpropyl)-2-chloro-5-[3,6-dihydro-2,6-dioxo-3-methyl-4-trifluoromethyl-1(2H)-pyrimidinyl]-4-fluorobenzamide,
N-cyclopropyl-2-chloro-5-[3,6-dihydro-2,6-dioxo-3-methyl-4-trifluoromethyl-1(2H)-pyrimidinyl]-4-fluorobenzamide,
N-cyclohexyl-2-chloro-5-[3,6-dihydro-2,6-dioxo-3-methyl-4-trifluoromethyl-1(2H)-pyrimidinyl]-4-fluorobenzamide, N-benzyl-2-chloro-5-[3,6-dihydro-2,6-dioxo-3-methyl-4-trifluoromethyl-1(2H)-pyrimidinyl]-4-fluorobenzamide, N-(1-phenylethyl)-2-chloro-5-[3,6-dihydro-2,6-dioxo-3-methyl-4-trifluoromethyl-1(2H)-pyrimidinyl]-4-fluorobenzamide, N,N-diethyl-2-chloro-5-[3,6-dihydro-2,6-dioxo-3-methyl-4-trifluoromethyl-1(2H)-pyrimidinyl]-4-fluorobenzamide, N-allyl-2-chloro-5-[3,6-dihydro-3,4-dimethyl-2,6-dioxo-1(2H)-pyrimidinyl]-4-fluorobenzamide, N-(1-cyano-1-methylethyl)-2-chloro-5-[3,6-dihydro-3,4-dimethyl-2,6-dioxo-1(2H)-pyrimidinyl]-4-fluorobenzamide, N-allyl-2-chloro-5-[3,6-dihydro-2,6-dioxo-3-methyl-4-pentafluoroethyl-1(2H)-pyrimidinyl]-4-fluorobenzamide and N-allyl-2-chloro-5-[3,6-dihydro-3,4-dimethyl-2,6-dioxo-1(2H)-pyrimidinyl]-benzamide.

9. A compound according to claim 1, which is N-allyl-2-chloro-5-[3-difluoromethyl-3,6-dihydro-2,6-dioxo-4-methyl-1-(2H)-pyrimidinyl]-4-fluorobenzamide.

10. A weed control composition, characterized in that it contains an effective amount of at least one compound of the formula

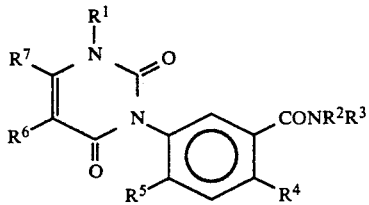

I wherein
- $R^1$ signifies hydrogen, $C_{1-4}$-alkyl, $C_{1-4}$-haloalkyl, $C_3$ or 4-alkenyl or $C_3$ or 4-alkynyl,
- $R^2$ and $R^3$ each independently signify hydrogen, $C_{1-8}$-alkyl, $C_{2-8}$-alkenyl, $C_{3-8}$-alkynyl, $C_{1-8}$-haloalkyl, $C_{1-8}$-hydroxyalkyl, $C_{1-4}$-alkoxy-$C_{1-8}$-alkyl, $C_{1-4}$-alkylthio-$C_{1-8}$-alkyl, $C_{1-4}$-haloalkoxy-$C_{1-8}$-alkyl, $C_{2-8}$-cyanoalkyl, $C_{1-8}$-nitroalkyl, $C_{2-9}$-carboxyalkyl, $C_{2-5}$-alkoxycarbonyl-$C_{1-8}$-alkyl, $C_{1-4}$-alkylsulphonyl-$C_{1-8}$-alkyl, di($C_{1-4}$-alkyl)-phosphono-$C_{1-8}$-alkyl, $C_{3-8}$-cycloalkyl, $C_{1-8}$-alkoxy or phenyl or phenyl-$C_{1-4}$-alkyl optionally substituted with halogen, hydroxy, $C_{1-4}$-alkyl, $C_{1-4}$-haloalkyl, $C_{1-4}$-alkoxy, $C_{1-4}$-alkylthio, $C_{1-4}$-haloalkoxy, cyano, nitro, carboxy and/or $C_{2-5}$-alkoxycarbonyl, whereby this optionally substituted phenyl can have a fused, saturated, carbocyclic five- to seven-membered ring or a fused, saturated, heterocyclic five- to seven-membered ring containing 1 or 2 oxygen atoms, whereby $R^2$ and $R^3$ cannot both stand for $C_{1-8}$-alkoxy, or
- $R^2$ and $R^3$ together with the nitrogen atom to which they are attached signify a four- to seven-membered heterocyclic ring which is optionally mono- or multiply substituted with $C_{1-6}$-alkyl and which, in addition to the nitrogen atom, can also have in the ring an oxygen atom, a sulphur atom and/or a second nitrogen atom,
- $R^4$ signifies halogen or cyano,
- $R^5$ signifies hydrogen or halogen,
- $R^6$ signifies hydrogen, halogen or $C_{1-4}$-alkyl,
- $R^7$ signifies $C_{1-4}$-alkyl or, where $R^1$ is different from $C_{1-4}$-haloalkyl, also $C_{1-4}$-haloalkyl, or
- $R^6$ and $R^7$ together signify tri- or tetramethylene, or of an enol ether of such a compound in which $R^1$ signifies $C_{1-4}$-alkyl, $C_3$ or 4-alkenyl or $C_3$ or 4-alkynyl, $R^6$ signifies hydrogen, halogen or $C_{1-4}$-alkyl and $R^7$ signifies $C_{1-4}$-haloalkyl or of a salt of such a compound or of such an enol ether in which $R^1$ and/or $R^2$ signifies hydrogen, as well as formulation adjuvants.

11. A weed control composition according to claim 10, characterized in that it contains an effective amount of at least one compound selected from the group N-ethyl-2-chloro-5-[3,6-dihydro-2,6-dioxo-3-methyl-4-trifluoromethyl-1(2H)-pyrimidinyl]-4-fluorobenzamide, N-propyl-2-chloro-5-[3,6-dihydro-2,6-dioxo-3-methyl-4-trifluoromethyl-1(2H)-pyrimidinyl]-4-fluorobenzamide, N-isopropyl-2-chloro-5-[3,6-dihydro-2,6-dioxo-3-methyl-4-trifluoromethyl-1(2H)-pyrimidinyl]-4-fluorobenzamide, N-butyl-2-chloro-5-[3,6-dihydro-2,6-dioxo-3-methyl-4-trifluoromethyl-1(2H)-pyrimidinyl]-4-fluorobenzamide, N-(sec.butyl)-2-chloro-5-[3,6-dihydro-2,6-dioxo-3-methyl-4-trifluoromethyl-1(2H)-pyrimidinyl]-4-fluorobenzamide, N-allyl-2-chloro-5-[3,6-dihydro-2,6-dioxo-3-methyl-4-trifluoromethyl-1(2H)-pyrimidinyl]-4-fluorobenzamide, N-(2-methyl-2-propenyl)-2-chloro-5-[3,6-dihydro-2,6-dioxo-3-methyl-4-trifluoromethyl-1(2H)-pyrimidinyl]-4-fluorobenzamide, N-propargyl-2-chloro-5-[3,6-dihydro-2,6-dioxo-3-methyl-4-trifluoromethyl-1(2H)-pyrimidinyl]-4-fluorobenzamide, N-1,1-dimethyl-2-propynyl)-2-chloro-5-[3,6-dihydro-2,6-dioxo-3-methyl-4-trifluoromethyl-1(2H)-pyrimidinyl]-4-fluorobenzamide, N-(1-cyano-1-methylethyl)-2-chloro-5-[3,6-dihydro-2,6-dioxo-3-methyl-4-trifluoromethyl-1(2H)-pyrimidinyl]-4-fluorobenzamide, N-(1-cyano-1,2-dimethylpropyl)-2-chloro-5-[3,6-dihydro-2,6-dioxo-3-methyl-4-trifluoromethyl-1(2H)-pyrimidinyl]-4-fluorobenzamide, N-cyclopropyl-2-chloro-5-[3,6-dihydro-2,6-dioxo-3-methyl-4-trifluoromethyl-1(2H)-pyrimidinyl]-4-fluorobenzamide, N-cyclohexyl-2-chloro-5-[3,6-dihydro-2,6-dioxo-3-methyl-4-trifluoromethyl-1(2H)-pyrimidinyl]-4-fluorobenzamide, N-benzyl-2-chloro-5-[3,6-dihydro-2,6-dioxo-3-methyl-4-trifluoromethyl-1(2H)-pyrimidinyl]-4-fluorobenzamide, N-(1-phenylethyl)-2-chloro-5-[3,6-dihydro-2,6-dioxo-3-methyl-4-trifluoromethyl-1(2H)-pyrimidinyl]-4-fluorobenzamide, N,N-diethyl-2-chloro-5-[3,6-dihydro-2,6-dioxo-3-methyl-4-trifluoromethyl-1(2H)-pyrimidinyl]-4-fluorobenzamide, N-allyl-2-chloro-5-[3,6-dihydro-3,4-dimethyl-2,6-dioxo-1(2H)-pyrimidinyl]-4-fluorobenzamide, N-(1-cyano-1-methylethyl)-2-chloro-5-[3,6-dihydro-3,4-dimethyl-2,6-dioxo-1(2H)-pyrimidinyl]-4-fluorobenzamide, N-allyl-2-chloro-5-[3,6-dihydro-2,6-dioxo-3-methyl-4-pentafluoroethyl-1(2H)-pyrimidinyl]-4-fluorobenzamide and N-allyl-2-chloro-5-[3,6-dihydro-3,4-dimethyl-2,6-dioxo-1(2H)-pyrimidinyl]-benzamide as well as formulation adjuvants.

12. A weed control composition according to claim 10, characterized in that it contain an effective amount of N-allyl-2-chloro-5-[3-difluoromethyl-3,6-dihydro-2,6-dioxo-4-methyl-1(2H)-pyrimidinyl]-4-fluorobenzamide as well as formulation adjuvants.

* * * * *